United States Patent [19]
Bromberg et al.

[11] Patent Number: 5,753,832
[45] Date of Patent: May 19, 1998

[54] VAPOR AND PARTICLE SAMPLING

[75] Inventors: Edward E. A. Bromberg, Peabody; George B. Jarvis, Arlington; Karen E. LeBlanc, Dracut; Gregory J. Wendel, Somerville; Carlton Wong, Brighton; Ain A. Sonin, Lexington, all of Mass.

[73] Assignee: Thermedics Detection Inc., Chelmsford, Mass.

[21] Appl. No.: 966,922

[22] Filed: Nov. 10, 1997

Related U.S. Application Data

[63] Continuation of Ser. No. 334,257, Nov. 3, 1994, abandoned.
[51] Int. Cl.$^6$ ................................................. G01N 31/00
[52] U.S. Cl. ................................... 73/864.81; 73/864.24
[58] Field of Search ............................. 73/863.21, 864, 73/864.01, 864.21, 864.23, 864.24, 864.81, 1 G

[56] References Cited

U.S. PATENT DOCUMENTS

| | | | |
|---|---|---|---|
| 3,461,727 | 8/1969 | Everhard et al. | 73/421.5 |
| 3,731,464 | 5/1973 | Brumbaugh et al. | 55/270 |
| 3,748,905 | 7/1973 | Fletcher et al. | 73/421.5 R |
| 3,970,428 | 7/1976 | Barringer | 23/230 EP |
| 4,053,281 | 10/1977 | Carter | 23/230 PC |
| 4,111,049 | 9/1978 | Lerner et al. | 73/421.5 R |
| 4,220,452 | 9/1980 | Bray | 23/232 R |
| 4,242,107 | 12/1980 | Jenkins . | |
| 4,305,724 | 12/1981 | Micko | 23/232 E |
| 4,417,574 | 11/1983 | Talonn et al. | 128/205.12 |
| 4,467,038 | 8/1984 | Scott | 436/115 |
| 4,502,951 | 3/1985 | Koenig et al. | 209/21 |
| 4,531,398 | 7/1985 | Di Benedetto et al. | 73/1 G |
| 4,534,204 | 8/1985 | Bergquist | 73/1 G |

(List continued on next page.)

FOREIGN PATENT DOCUMENTS

| | | |
|---|---|---|
| 0 383 611 | 8/1990 | European Pat. Off. . |
| 1 185 401 | 1/1965 | Germany . |
| 57-79429(A) | 5/1982 | Japan . |
| 720 014 | 1/1978 | U.S.S.R. . |
| 2 262 603 | 6/1993 | United Kingdom . |

OTHER PUBLICATIONS

Jenkins et al., "Extraction, Transportation and Processing of Explosives Vapor in Detection Systems", Proceedings of the First International Symposium on Explosive Detection Technology Nov. 13–15, 1991, (Feb. 1992).
Bromberg et al., "Vapor Generation for Use in Explosive Portal Detection Devices," Advances in Analysis and Detection of Explosives, Mar. 1993, 473–484.
Fraim et al., "Efficient Collection of Explosive Vapors, Particles and Aerosols," Proceedings of the First International Symposium on Explosive Detection Technology, Feb. 1992, 559–565.
MacDonald et al., "Calibration Methods for Explosives Detectors," Proceedings of the First International Symposium on Explosive Detection Technology, Feb. 1992, 584–588.
Rounbehler et al., "Analysis of Explosives Using High Speed Gas Chromatography with Chemiluminescent Detection," Proceedings of the First International Symposium on Explosive Detection Technology, Feb. 1992, 703–713.

*Primary Examiner*—George M. Dombroske
*Assistant Examiner*—Max H. Noori
*Attorney, Agent, or Firm*—Fish & Richardson P.C.

[57] ABSTRACT

In a contact-type vapor and particle sampling apparatus for collecting vapor or particles from a moving subject, a wand having a plurality of sampling holes is oriented so that the holes extend in the direction of movement of the subject. The external width of the wand is less than a characteristic dimension of the contour of the surface of the subject being sampled, and a central fluid flow passage in the wand is sufficiently wide to prevent substantially all particles of on the order of about 10 microns in diameter from colliding with the wall of the wand as they enter the passage. A collector for use with the apparatus includes a gas impermeable material having a high binding affinity for explosives vapor exposed on a surface of a filter woven to trap explosives particles.

34 Claims, 12 Drawing Sheets

U.S. PATENT DOCUMENTS

| | | | |
|---|---|---|---|
| 4,909,090 | 3/1990 | McGown et al. | 73/864.33 |
| 4,964,309 | 10/1990 | Jenkins | 73/864.81 |
| 4,987,767 | 1/1991 | Corrigan et al. | 73/23.36 |
| 5,040,424 | 8/1991 | Marple et al. | 73/863.23 |
| 5,090,257 | 2/1992 | Bruce | 73/863.03 |
| 5,092,155 | 3/1992 | Roundbehler et al. | 73/1 G |
| 5,092,217 | 3/1992 | Achter et al. | 86/1.1 |
| 5,109,691 | 5/1992 | Corrigan et al. | 73/23.36 |
| 5,345,809 | 9/1994 | Corrigan et al. | 73/23.2 |
| 5,355,719 | 10/1994 | Kohsaka et al. | 73/31.07 |
| 5,455,007 | 10/1995 | Calvo et al. | 73/864.21 |
| 5,465,607 | 11/1995 | Corrigan et al. | 73/23.36 |
| 5,493,890 | 2/1996 | Dussault et al. | 73/1 G |

VAPOR AND PARTICLE SAMPLING

This application is a continuation of Ser. No. 08/334,257 filed Nov. 3, 1994 now abandoned

STATEMENT AS TO FEDERALLY SPONSORED RESEARCH

This invention was made with Government support under Contract DTFA-03-87-C-00003. The Government has certain rights in this invention.

BACKGROUND OF THE INVENTION

The present invention relates to vapor and particle collection systems.

When substances such as explosives are handled, minute particles of the substance, which typically have diameters on the order of about 10 microns, often become lodged in nearby areas, including the handler's hair, skin, and clothing. And even when wrapped tightly and stored, most substances emit a certain degree of vapor, the extent of the vaporization depending on such factors as the ambient temperature and the vapor pressure of the substance.

Systems for collecting, or sampling, vapor and particles, for example explosives vapors and/or particles from a person or piece of luggage, are typically either of two general types: non-contact and contact. In non-contact collection systems, a stream of air is typically passed over the subject, intermixing with vapor emanating from the subject and dislodging particles trapped on the subject's skin, clothing, hair, etc. The sample air stream carries the entrained vapors and/or particles to a collection region, where the sample air is channelled to a sample collector. The sample collector generally includes a large surface area desorb site, configured and treated to have a high affinity for the substance or substances of interest.

Sample collectors are described in U.S. Pat. No. 5,092,217, issued to Achter et al., assigned to the present assignee, and incorporated herein by reference in its entirety. As the sample air flows over the desorb site, at least a portion of the entrained vapor and/or particles collects on the surface. The sample collector is then later processed, for example by heating the site to vaporize, or desorb, the particles and vapors collected thereon. The resulting desorb air may then be analyzed, for example in a high-speed gas chromatograph, to assess whether the subject is carrying or contains the substance of interest.

Contact vapor and particle sampling systems operate on a similar principle, except a vacuum nozzle in the system is typically brought into direct contact with a surface of the subject. When vacuum is applied, sample air is collected from the immediate vicinity of the nozzle, drawing vapor and/or particles into the system for collection.

SUMMARY OF THE INVENTION

One general aspect of the invention is a contact-type vapor and particle sampling apparatus for collecting vapor or particles from a moving subject, in which a wand having a plurality of sampling holes is oriented so that the holes extend in the direction of movement of the subject.

Among other advantages, because the sampling holes extend in the direction of movement of the subject, the subject can be sampled by successive holes or groups of holes while the subject moves through the apparatus. Thus, for instance, if the wand is sufficiently long and provided with a sufficient number of holes, a person walking at a normal pace would just pass through the apparatus in the time necessary to execute a single sampling cycle. As the subject moves along the wand, successive sampling holes are sequentially covered and uncovered, one or more holes always remaining in contact with, or in close proximity to, the subject. In this manner, sampling can be accomplished without disturbing the normal flow of the subjects, be they passengers walking through an airport or baggage or other items travelling along a conveyor belt, making the sampling process less cumbersome and intrusive.

Preferred embodiments include the following features.

In a particularly useful embodiment, a plurality of wands are pivotally attached to a housing. The wands, e.g., curved tubular sections of polyvinyl chloride pipe, are angled downward and are biased towards one another. As the subject (e.g., a person) moves between them, the wands separate, but remain in contact with the person's body. A damper damps the rotation of the wands, providing increased resistance as the subject moves more quickly through the apparatus.

Sample air collected through the sample holes, which are disposed at different rotational orientations around the circumferences of the wands, is delivered through a central fluid flow passage to a vapor and particle collector (e.g., a collector configured for use with an explosives vapor analyzer). A valve in a bypass line connected upstream of the collector can be adjusted to divert a portion of the sample air before it reaches the collector. Because of the bypass line, the aggregate flow rate through the wands can exceed the flow rate through the collector. The flow rate through the wands thus is not directly constrained by the maximum flow rate through the collector. The flow rates through the wands therefore can be increased as necessary, for example to reduce the number of particles that collide with the inner surfaces of the wands.

In another aspect of the invention, the external width of a wand in a contact-type vapor and particle sampling apparatus is less than a characteristic dimension of the contour of the surface of the subject being sampled.

Among other advantages, when sampling an irregularly shaped subject, such as a person, the wand, and thus also the sampling holes in the wand, remain in much closer contact with the surface of the subject than would a wider wand, improving sampling effectiveness. Where the invention is to be used to sample people, because of the surface contour characteristics of the average person, generally the width of the wand (e.g., the wand outer diameter if the wand is tubular) is below about 4 in. (10 cm.), and is preferably on the order of about 1 to 2 in. (2.5 to 5 cm.).

In another aspect of the invention, the central fluid flow passage in a wand in a contact-type vapor and particle sampling apparatus is sufficiently wide to prevent substantially all of the particles of on the order of about 10 microns in diameter from colliding with the wand walls.

Should they collide with the inside wall of the wand, particles very frequently stick to the wall surface, and thus may not be carried to the collector. By preventing a substantial percentage of particles from colliding with the wall, this aspect of the invention thus advantageously increases the percentage of particles delivered to the collector. Moreover, the invention reduces the likelihood that a particle will stick to the wall during one sampling cycle, and dislodge during a subsequent sampling cycle, thereby possibly making the first reading erroneously low, and the second erroneously high.

In preferred embodiments of this aspect of the invention, the sampling holes lie at an acute angle to the central passage. Particles thus enter the central passage travelling in a direction that is nearly aligned with the direction of the airflow through the passage, further reducing the likelihood that entering particles will travel across the passage and strike the opposite wall. In addition, an orifice disposed in one end of the central fluid flow passage regulates to a large degree the flow rate through the wand. The higher the flow rate, the less the chance that entering particles will travel across the passage and strike the opposite wall.

In another aspect of the invention, two symmetrically disposed arrays of sampling wands are disposed at an acute angle to the direction of movement of the subject, traversing a surface of the subject as the subject moves through the apparatus.

Among other advantages, the arrays of sampling wands sweep downward across the subject as the subject moves, sampling vapors and particles from entire vertical regions.

Another aspect of the invention is a collector that includes a gas impermeable material having a high binding affinity for explosives vapor exposed on a surface of a filter woven to trap explosives particles. The collector advantageously collects at least a portion of the explosives vapors and particles entrained in the airstream flowing therethrough.

In preferred embodiments of this aspect of the invention, the filter paper is held in a frame, and the gas impermeable material comprises polyimide strips arranged on the surface of the filter paper.

Other features and advantages of the invention will become apparent from the following detailed description, and from the claims.

DESCRIPTION OF THE PREFERRED EMBODIMENT(S)

Figure 1:
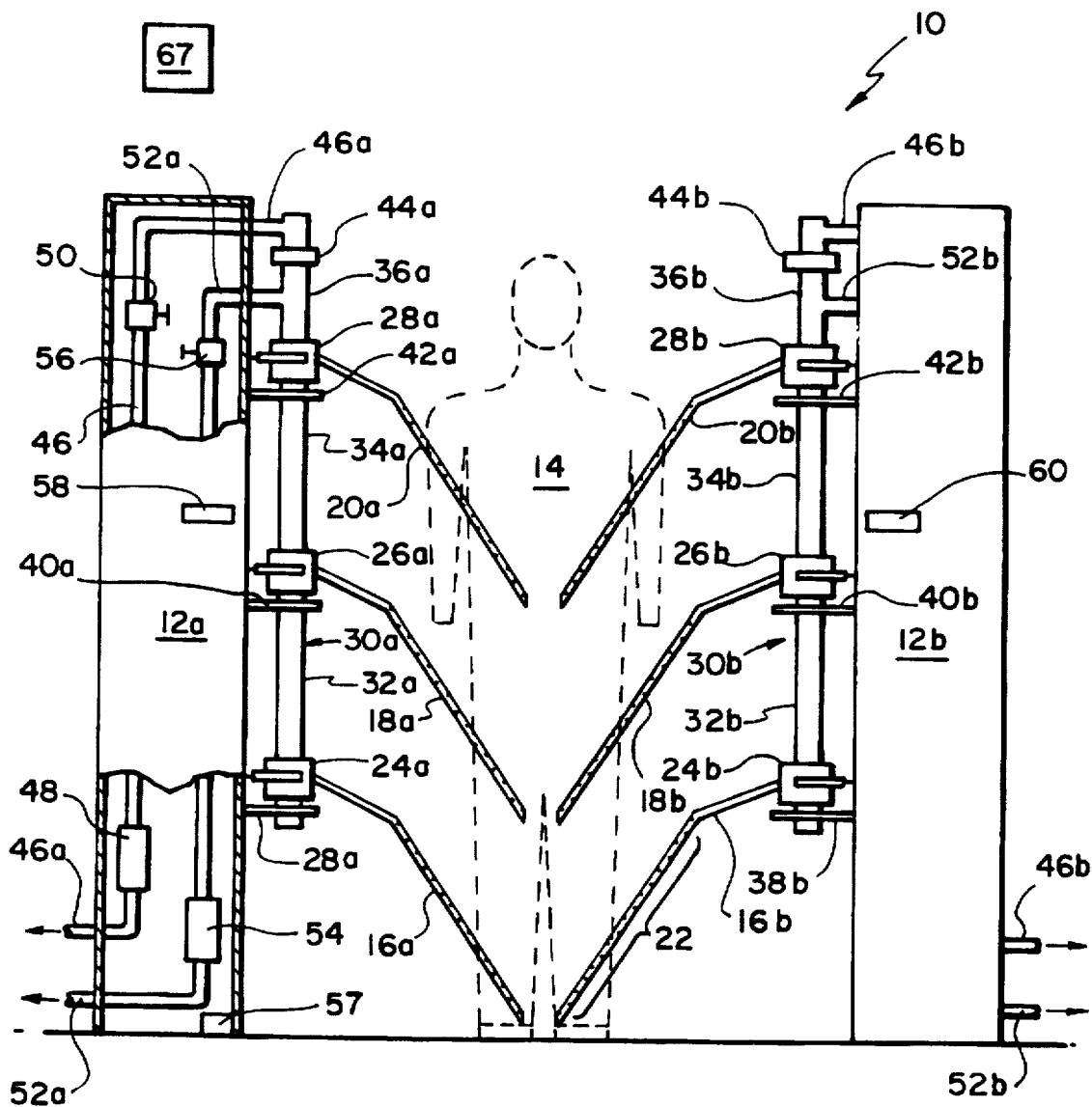
FIG. 1 is a partially cut away front view of an explosives sampling system.

As shown in FIG. 1, an explosives vapor and particle collection system 10 includes two vertically extending housings 12a, 12b, between which a person 14 to be sampled walks or is moved, e.g., by a endless-belt conveyor (not shown). Housing 12a, and its associated components, are a mirror image of housing 12b and its associated components. For convenience, like components are assigned the same numerical label, with the suffix "a" appended to the numeral corresponding to the component that lies in the left half of system 10, and the suffix "b" appended to the numeral corresponding to the component that lies in the right half of system 10.

Figure 2:
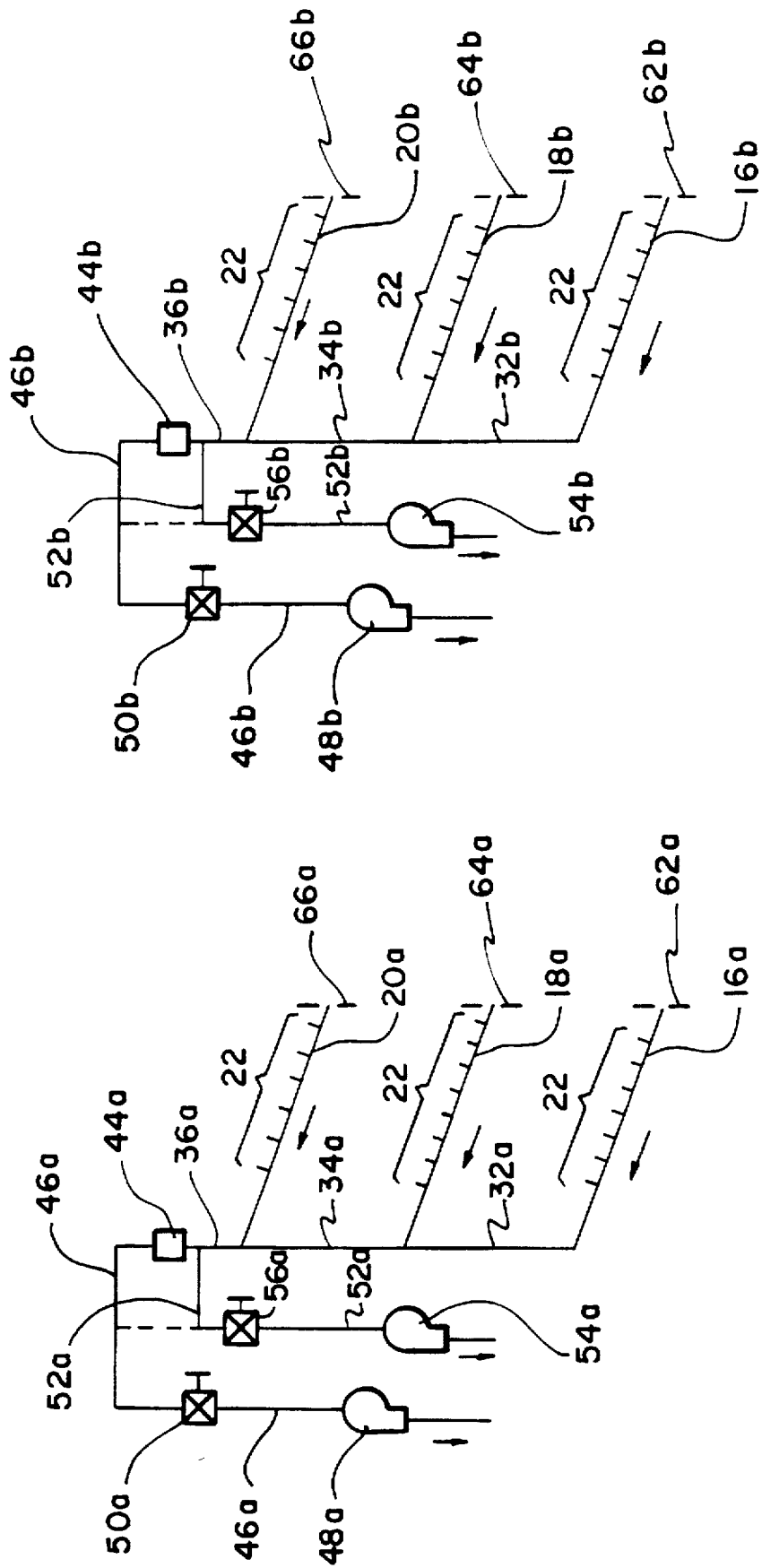
FIG. 2 is a schematic of the explosives sampling system of FIG. 1.

With reference also to FIG. 2, each housing 12a, 12b supports an array of three pivotally mounted, finger-like wands 16a, 18a, 20a; 16b, 18b, 20b. Each wand is a thin, curved tube, for example of polyvinyl chloride, that includes a plurality of holes 22 oriented to sweep over the outer surface of person 14 as he or she walks through the system. (For convenience, the collective plurality of holes in each wand are indicated by a single reference numeral, 22. When specific holes are discussed, they are given unique reference numerals.)

Figure 8:
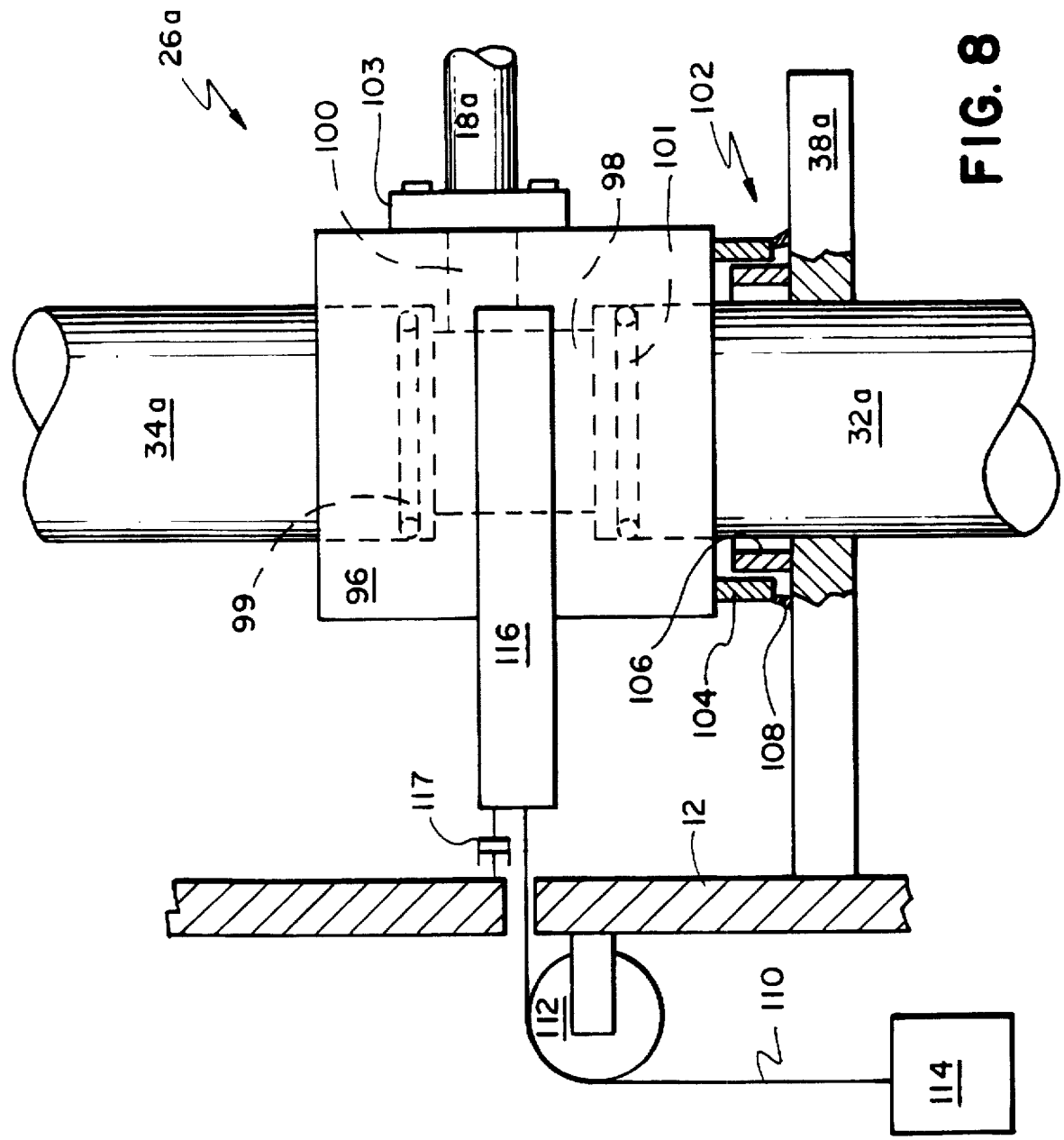
FIG. 8 is a partially cut away front view of a pivot mechanism for use with the explosives sampling system of FIG. 1.

Each wand connects at one end to a pivot assembly 24a, 26a, 28a; 24b, 26b, 28b. As described in detail below in connection with FIG. 8, pivot assemblies 24a, 26a, 28a; 24b, 26b, 28b allow the wands to pivot with respect to manifold assemblies 30a, 30b supported by housings 12a, 12b, while keeping the hollow interior of each wand in fluid communication with the hollow interior of the associated manifold assembly. Manifold assemblies 30a, 30b, which are parallel to one another and separated by approximately 30 in. (0.75 m.) to allow person 14 to pass therebetween, are each constructed of three segments of pipe 32a, 34a, 36a; 32b, 34b, 36b, also of polyvinyl chloride. The pipe segments are supported by support arms 38a, 40a, 42a; 38b, 40b, 42b, which are cantilevered from the sides of housings 12a, 12b.

The uppermost segment 36a, 36b of each manifold assembly 30a, 30b is a T-section of pipe, having a horizontal branch in fluid communication with upper and lower vertical branches. The upper vertical branch of each of uppermost segments 36a, 36b sealably and releasably mates with the inlet of a sample collector 44a, 44b. Sample collectors, which collect at least a portion of the vapor and particles entrained in the airstreams flowing therethrough, are described in U.S. Pat. No. 5,092,217, issued to Achter et al., assigned to the present assignee, and incorporated herein by reference in its entirety. The outlet of each of collectors 44a, 44b sealably and releasably mates with a collector exhaust line 46a, 46b. A vacuum blower 48a, 48b in each collector exhaust line 46a, 46b draws sample air through the collectors 44a, 44b, and a valve 50a, 50b in each collector exhaust line 46a, 46b is adjustable to control the flow rate through the collectors (vacuum blower 48b and valve 50b in collector exhaust line 46b are not shown in FIG. 1).

The horizontal branches of uppermost segments 36a, 36b are sealably coupled to respective bypass lines 52a, 52b. Similar to collector exhaust lines 46a, 46b, a vacuum blower 54a, 54b draws bypass air through each bypass line, and a valve 56a, 56b in the lines may be adjusted to vary the flow rate of bypass air through the lines (vacuum blower 54b and valve 56b in bypass line 52b are not shown in FIG. 1).

The vacuum blowers in collector exhaust lines 46a, 46b and bypass lines 52a, 52b are controlled by a controller unit 57 in housing 12a. When triggered by a sample cycle initiation signal, generated when a detector 58 mounted to housing 12a detects that a light beam emitted by an emitter 60 mounted to housing 12b has been broken, controller unit 57 activates the blowers for a predetermined sampling cycle time.

In operation, when person 14 passes the front edges of housings 12a, 12b from the side shown in FIG. 1, he or she breaks the beam of light generated by emitter 60, initiating the sampling cycle. During the sampling cycle, vacuum blowers 48a, 48b, 54a, 54b draw outside air (i.e., from atmosphere) through holes 22 in the sides of the wands, as well as through orifices 62a, 64a, 66a; 62b, 64b, 66b in the free ends of wands 16a, 18a, 20a; 16b, 18b, 20b. The aggregate flow rate through each three-wand array is typically on the order of 20 liters/second. Valves 50a, 50b, 56a, 56b can be adjusted to select the proportion of the sample air drawn into manifold assemblies 30a, 30b that flows through collectors 44a, 44b. Typically, the valves are adjusted to allow approximately half of the flow to pass through bypass lines 52a, 52b, and half to pass through collectors 44a, 44b. When the sampling cycle concludes, collectors 44a, 44b are removed from system 10 and processed in an explosives vapor and particle analyzer 67 (shown schematically in FIG. 1) to determine the explosives content of the sample air drawn from person 14.

Figure 3:
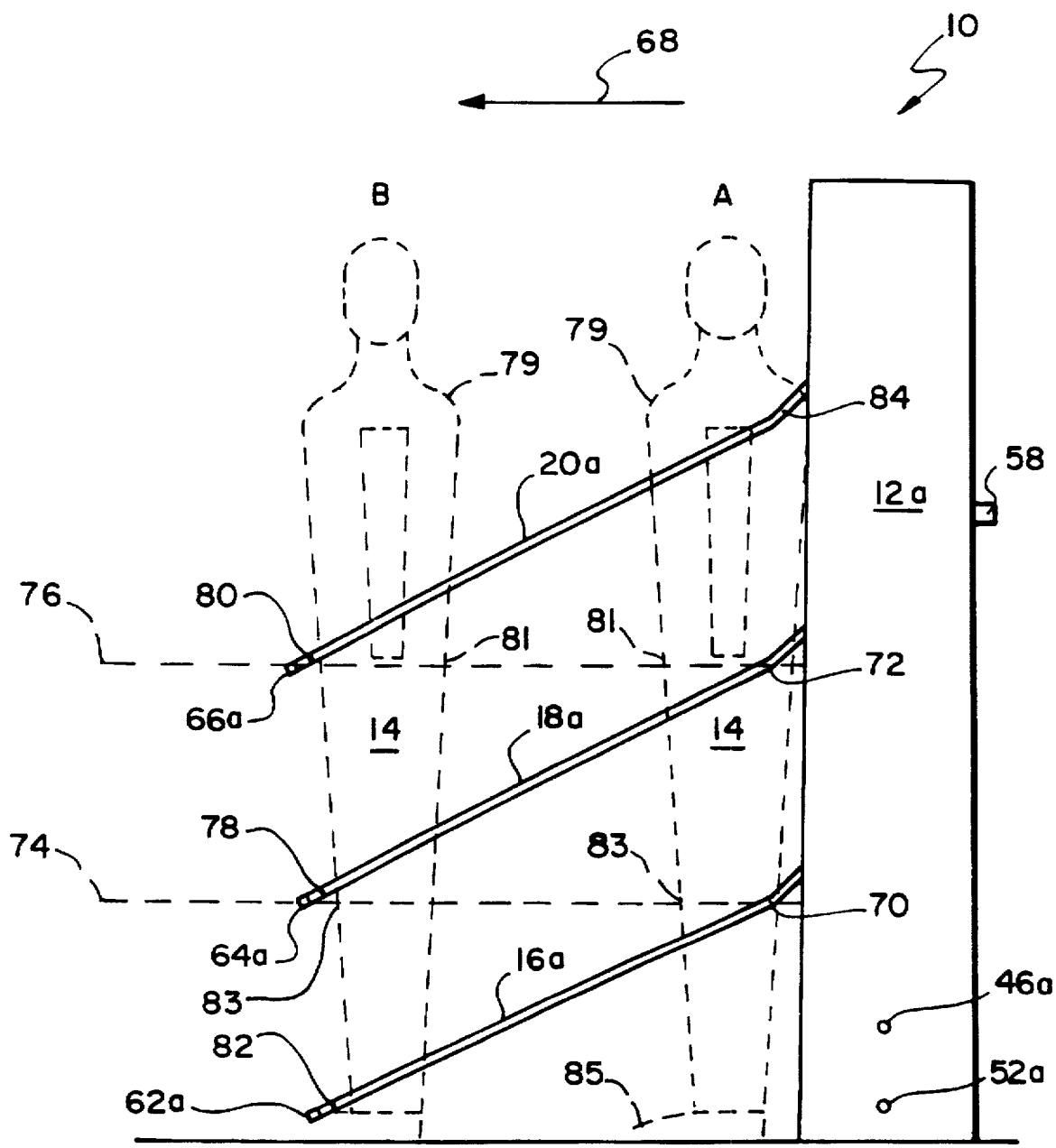
FIG. 3 is a side view of the explosives sampling system of FIG. 1.

System 10, and in particular wands 16a, 18a, 20a, 20b, are shown in further detail in FIGS. 3 and 4. As illustrated in FIG. 3, the wands are angled downward, lying at an acute, approximately 30°, angle to the direction of movement of person 14, indicated in FIGS. 3 and 4 by arrow 68. Wands 16b, 18b, 20b (not shown in FIG. 3) are similarly oriented. The wand angle is chosen such that the first holes 70, 72 (i.e., the holes closest to housing 12a) in wands 16a, 18a lie in approximately the same horizontal planes 74, 76 as the last holes 78, 80 (i.e., the holes farthest from housing 12a) in wands 18a, 20a, the wands directly above wands 16a, 18a, respectively. (For clarity, although they lie on the side opposite the side shown, the holes in wands 16a, 18a, 20a are not shown in phantom in FIG. 3.) The last hole 82 in wand 16a lies close to the ground, and the first hole 84 in wand 20a lies in or near the same horizontal plane as the shoulder 79 of person 14. Other holes (not shown) lie at regular intervals between the first and last holes in each wand.

When person 14 first enters system 10 (i.e., when person 14 is in position A), holes 70, 72, 84 in wands 16a, 18a, 20a are at his knees 83, waist 81, and shoulders 79, respectively. And when person 14 is near the end of wands 16a, 18a, 20a (i.e., when person 14 is in position B), holes 82, 78, and 80 in wands 16a, 18a, 20a are at his feet 85, knees 83, and waist 81, respectively. Thus, as person 14 moves in the direction indicated by arrow 68, successive holes (not shown) in the wands make contact with progressively lower portions of his body. In essence, as person 14 walks through the system 10, the wands sweep vertically down his sides (or, if he rotates 90°, his front and back), sampling different regions of his clothing, skin, hair, etc.

Several considerations factor into the selection of the lengths of wands 16a, 18a, 20a; 16b, 18b, 20b. As noted above, the sampling cycle lasts for a predetermined time, generally 4 or 5 seconds. Preferably, the wands are long enough that a person walking at a normal pace just passes through system 10 in the time it takes to execute a single sampling cycle. However, as wand length increases, the wands can become difficult to support at only one end. Balancing these considerations, a wand length of around 60 in. (1.5 m.) has been found to be suitable for many applications.

Figure 4A:
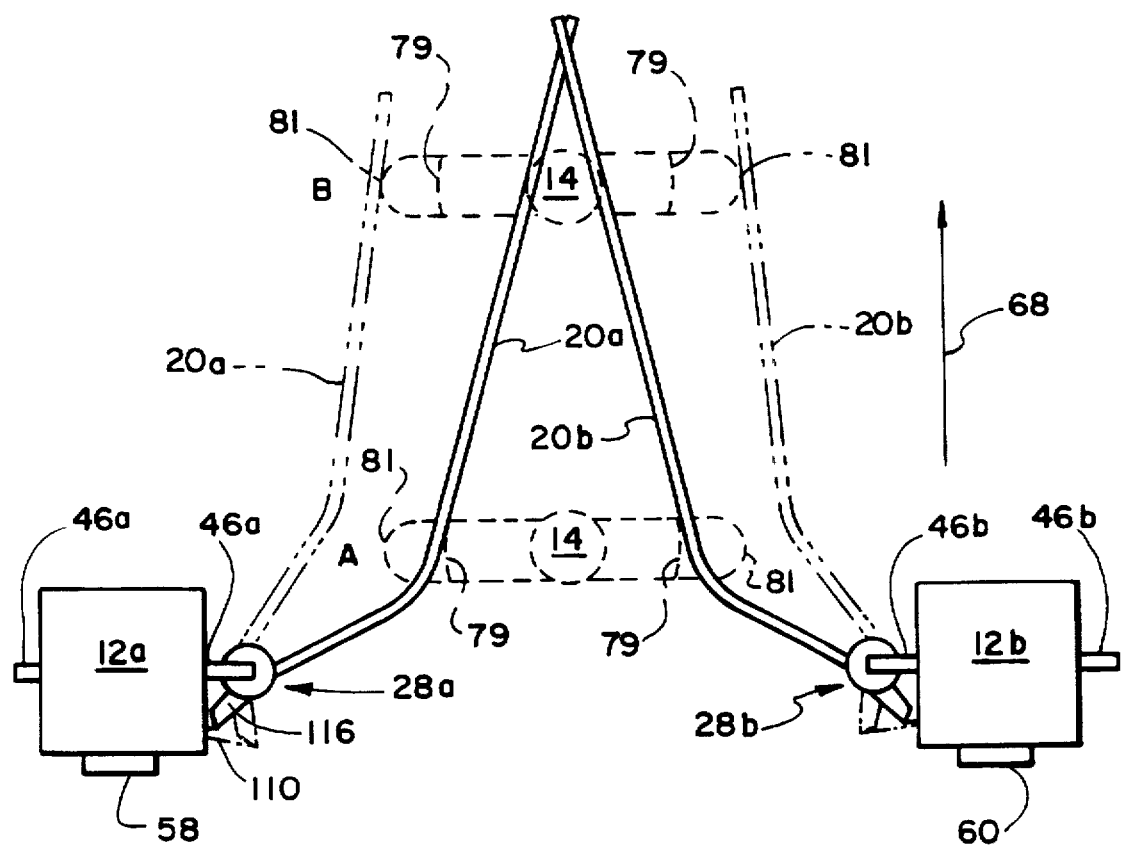
FIG. 4a is a top view of the explosives sampling system of FIG. 1.

As shown in FIG. 4a, when viewed from the top, wands 20a, 20b are curved and angled toward one another, forming a funnel-shaped region that receives person 14, and guides him through system 10. Wands 16a, 18a, 16b, 18b (not shown in FIG. 4a) are similarly curved and angled. As explained in detail below in connection with FIG. 8, the wands, although pivotable, are biased towards one another (the rest position of the wands is shown in solid lines in FIG. 4a). Thus, although person 14 forces the wands apart as he moves in the direction indicated by arrow 68, the wands (and thus holes 22 in the wands) remain in close contact with the person, following the contour of his body as they sweep downward. For instance, if the person's waist 81 is wider than his shoulders 79, wands 20a, 20b are forced apart less when he first enters system 10 (position A) than when he has nearly exited the system (position B; the position of wands 20a, 20b when person 14 is in position B is shown in phantom in FIG. 4a). The free ends of the wands 20a, 20b are crossed, which tends in some circumstances to improve the contact between the wands and person 14.

Figure 4B:
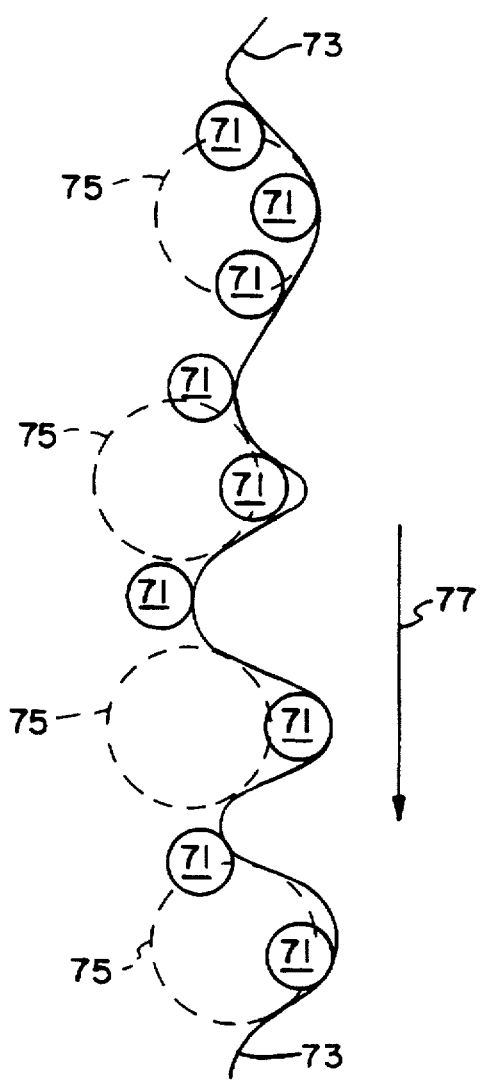
FIG. 4b is a schematic view of wands of two different sizes passing over an irregular surface.

It can thus be seen that it may be desirable to select the outside diameter of wands 16a, 18a, 20a; 16b, 18b, 20b in accordance with the characteristics of the contours of the surfaces of the subject to be sampled. Most surface contours can generally be described as a series of alternating peaks and valleys of varying radii. If the wand radius is larger than the characteristic dimension of the surface contour, i.e., the mean radius of the valleys, or recesses, in the surface contour, then the wands may ride along the top of the peaks as the wands move downward over the surface, preventing the holes in the wands from coming into direct contact with a significant portion of the surface. This is schematically shown in FIG. 4b, which illustrates how a smaller wand 71 remains in closer contact with the small-radius portions of irregular surface 73 than a larger wand 75 (shown in phantom) as the two wands sweep down the surface in the direction indicated by arrow 77. The holes in wands 73, 75 are substantially perpendicular to the direction indicated by arrow 77, and are directed toward surface 73. As illustrated, small wand 71 (and thus also the sampling holes in the wand) follows the contour of surface 73 much more closely than large wand 75, getting into a greater number of tight-radius areas. In the case of people, the peaks and valleys of surface 73 might, for example, represent regions where extremities bend or are attached to the body, as well as wrinkles and other surface irregularities in the sample subject's clothing. If the wands are sufficiently rigid and of relatively small diameter, because clothing and body tissue are generally fairly compliant, small surface irregularities in the subject's body or clothing typically yield to the wands.

In any event, because the effectiveness of a contact vapor and particle sampling system is generally improved by making direct, intimate contact with the surface to be sampled, if the wand diameter is too large, sampling effectiveness may be compromised. Accordingly, when people are to be sampled using system 10, to ensure good contour following, it is generally preferable if the outside diameter of the wands is less than about 4 in. (10 cm.). Wands around about 1 in. (2.5 cm.) have been found to be suitable.

Figure 5:
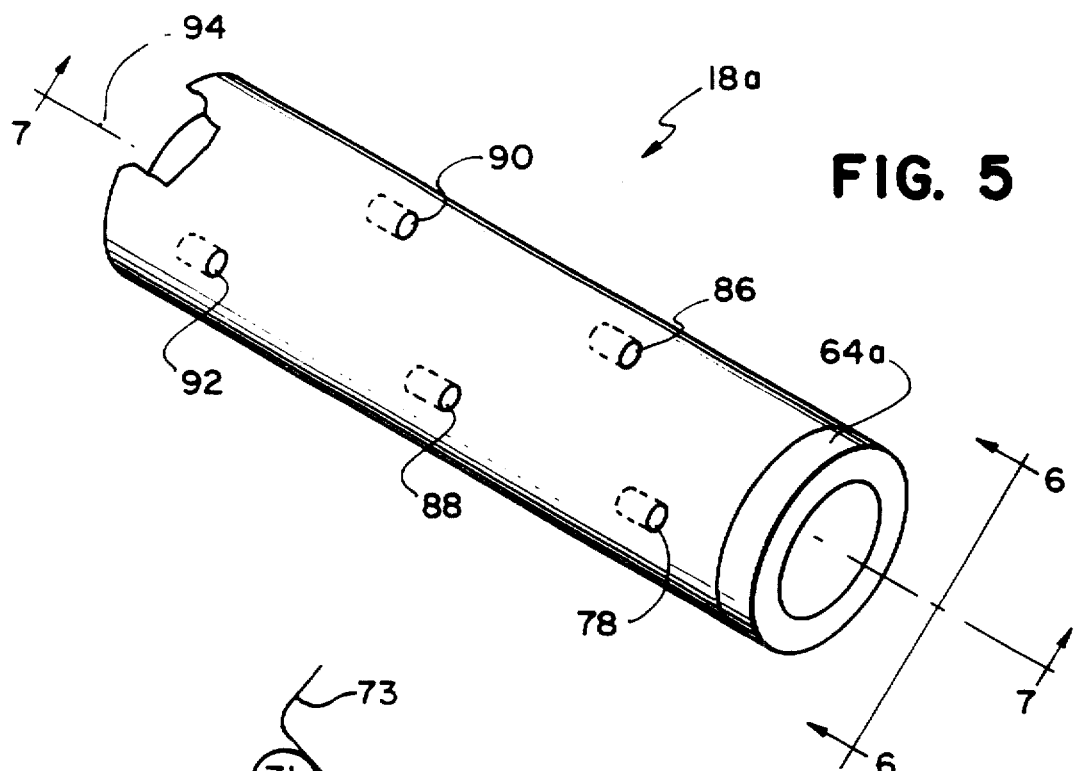
FIG. 5 is a detail perspective view of the free end of a wand for use with the explosives sampling system of FIG. 1.
Figure 6:
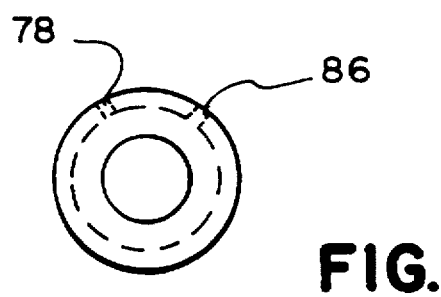
FIG. 6 is an end view taken along the line 6—6 in FIG. 5.
Figure 7:
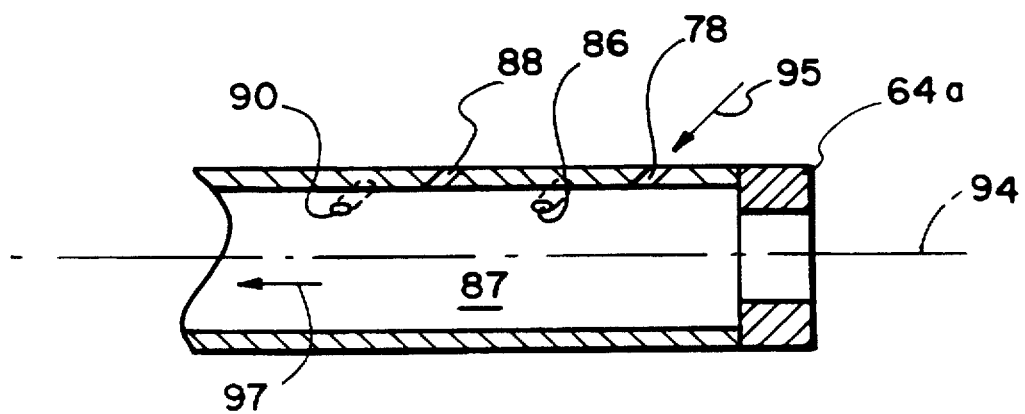
FIG. 7 is a sectional view taken along the line 7—7 in FIG. 5.

The free end of wand 18a is shown in detail in FIGS. 5, 6, and 7, and is representative of the free ends of wands 16a, 20*a*, 16*b*, 18*b*, 20*b*. The hollow interior 87 of wand 18*a* extends along the curved, longitudinal axis 94 of the wand, providing a fluid flow passage for conveying sample air drawn through the holes in the wand to manifold assembly 30*a*, and eventually to collector 44*a*. As exemplified by holes 78, 86, 88, 90, 92, the holes 22 (FIGS. 1 and 2) in the wall of wand 18*a* are spaced at regular intervals along the length of the wand, spanning between the first hole 72 (FIG. 3) and the last hole 78 in the wand. Thus, holes 22 in wands 16*a*, 18*a*, 20*a*; 16*b*, 18*b*, 20*b* extend in the direction of movement of person 14, indicated by arrow 68 (FIGS. 3 and 4). As person 14 walks through system 10, he or she sequentially covers and uncovers successive holes 22, and is thus at any given time sampled by only one or a few holes.

The diameter of the holes are typically selected in accordance with the desired fluid flow properties of the system. Generally speaking, increasing the diameter increases the flow rate through the hole, but decreases the pressure drop across the hole (i.e., the pressure drop between hollow interior 87 and atmosphere). Holes that are about 0.10 in. (2.5 mm.) in diameter have been found to be suitable for many applications.

The hole diameter also determines to some degree the spacing between adjacent holes. The smaller the hole diameter, the greater the total number of holes that can be made in each wand, and thus the more densely spaced the holes can be. For holes that are about 0.10 in. (2.5 mm.) in diameter, hole spacings between 1 and 2 in. (2.5 and 5 cm.) have been found to be suitable for many applications.

To improve the chances that at least some of them will make contact with the person's clothing, skin, etc., the holes are staggered, that is, adjacent holes are located at different rotational orientations around the circumference of wand 18*a*. For instance, holes 72, 88, 92 are at one rotational orientation, and holes 86, 90 are at another. Of course, all of the holes 22 in the six wands are located in the sides of the wands directed toward person 14. Moreover, because wands 16*a*, 18*a*, 20*a*; 16*b*, 18*b*, 20*b* are round, the exterior surfaces of the wands slope away on either side of holes 22, increasing the likelihood that the holes will make direct, intimate contact with the clothing, skin, etc. of person 14. Wands with similar cross-sections, such as ovoid or elliptical, can also be employed in system 10.

Holes 72, 86, 88, 90, 92 lie at an acute, approximately 45°, angle to axis 94. As noted above, sample air drawn through the holes may include explosives vapors and particles. When it enters hollow interior 87, the sample air is traveling in the direction indicated by arrow 95 in FIG. 7, a direction oblique the direction of the airflow through hollow interior 87, indicated by arrow 97 in FIG. 7. The incoming sample air therefore changes direction after entering hollow interior 87.

Because it is in a gaseous state, explosives vapor tends to change direction more readily than explosives particles, which typically have greater momentum. Thus, depending on its mass and velocity, there is a chance that an entering particle of explosives may not change direction quickly enough, and may travel across hollow interior 87 and strike the opposite inside wall of the wand. Should this occur, and should the particle stick to the inner wall, not only would the particle not be collected by the collector, possibly resulting in an erroneously low reading, but it could vaporize or dislodge during a subsequent sampling cycle, possibly resulting in an erroneously high reading. And should a sufficient number of particles become stuck to the inner surfaces of the wands, the wands may become so contaminated that have to be discarded. By angling holes 72, 86, 88, 90, 92, particles enter hollow interior 87 travelling in a direction 95 that is much more aligned with the direction of the main airflow 97, decreasing the chance that they will travel across the hollow interior and strike the opposite wall.

Other factors also influence the statistical probability that incoming particles will strike the opposite interior wall of the wands. One is the interior diameter of the wands. Increasing the inner diameter decreases the surface-area-to-volume ratio of the wand interiors, reducing the likelihood that incoming particles will strike the interior wall of the wands. To some degree, the wand inner diameter may be constrained by the desire to keep the outer diameter small to have good contour-following characteristics, as discussed above. Generally, the inner diameter will be increased as large as possible, consistent with the outer diameter of the wand, without unduly compromising the structural strength and rigidity of the wand. It is generally preferable to have a wand inner diameter greater than about 0.4 in. (1.0 cm.). Where the outside diameter of the wand is about 1 in. (2.5 cm.), a wand inner diameter of around 0.8 in. (2.0 cm.) has been found to be suitable for many applications.

The probability that incoming particles will strike the inner wall of the wands is also reduced by increasing the flow rate of the air traveling in the direction indicated by arrow 97 through the hollow interior of the wand. For a given vacuum blower throughput, the flow rate through the wands can be tailored to some degree by varying the size of the orifices 62*a*, 64*a*, 66*a*; 62*b*, 64*b*, 66*b* in the respective free ends of the wands. Generally speaking, increasing the orifice diameter increases the flow rate through the orifice, thus also increasing the cross-current flow rate through the wands. This tends to reduce the number of particles that collide with the interior surfaces of the wands. However, increasing orifice diameter also decreases the pressure drop across holes 22 (i.e., the pressure drop between hollow interior 87 and atmosphere), diminishing the vigor with which the holes vacuum the subject's skin, clothing, etc. Balancing these considerations, where the inside diameter of the wand is around 0.8 in. (2.0 cm.), and the holes are on the order of 0.10 in. (2.5 mm.) in diameter, an orifice diameter of around 0.6 in. (1.5 cm.) has been found to be suitable for many applications.

Pivot assembly 26*a*, which connects wand 18*a* to housing 12*a*, is shown in detail in FIG. 8. Pivot assemblies 24*a*, 28*a*, 24*b*, 26*b*, 28*b* are of similar construction to pivot assembly 26*a*. Pivot assembly 26*a* includes a sleeve 96 having an internal, spool-shaped cavity 98 that extends the length of the sleeve. The large-diameter regions of cavity 98 are slightly larger in diameter than the outer diameters of pipe segments 32*a*, 34*a*. With the pipe segments 32*a*, 34*a* inserted into the ends of cavity 98, sleeve 96 can be rotated with respect to the segments. O-rings 99, 101 on the ends of the pipe segments 32*a*, 34*a* maintain a substantially airtight seal between pivot assembly 26*a* and manifold assembly 30*a*. A flange 103 on the end of wand 18*a* bolts against the outside of sleeve 96, so that the internal passage of wand 18*a* is in fluid communication with a passage 100 in sleeve 96 that extends to cavity 98. Wand 18*a* can thus be easily unbolted and replaced should it become worn, contaminated with explosives particles, or otherwise unusable.

In order to prevent sleeve 96, and thus also wand 18*a*, from rotating too quickly, a rotary damper 102 is attached between sleeve 96 and support arm 38*a*. The rotor portion 104 of the damper is attached to the sleeve, and the stator portion 106 to arm 38*a*. A viscous fluid, such as an oil, fills the gap between rotor 104 and stator 106, and a seal 108 between rotor 104 and arm 38*a* prevents the fluid from escaping. The damping coefficient of rotary damper 102 is selected so that person 14 encounters substantial resistance if he attempts to pass through system 10 too quickly, but little resistance if he proceeds at a pace that allows the wands to contact his body throughout the sampling cycle.

As noted above, wands in the same horizontal plane are biased towards one another. This is accomplished gravitationally, by a cable 110 that extends over a pulley 112 between a weight 114 and an arm 116 attached to sleeve 96 (see also FIG. 4a). Rotating wand 18a and sleeve 96 from the rest position causes weight 114 to rise, urging the wand and sleeve back to the rest position. The weight-cable-pulley assembly could be replaced with a spring, either a linear spring between arm 116 and housing 12, or a torsional spring between sleeve 96 and arm 38a. In addition to or instead of rotary damper 102, a linear damper or dashpot 117 (shown schematically in FIG. 8), such as a gas spring, can be installed between arm 116 and housing 12.

Other embodiments are within the claims.

For instance, instead of using a separate sample collector for each side of the system, a single collector arranged to receive at least a portion of the flow from both manifold assemblies could be used.

Figure 9:
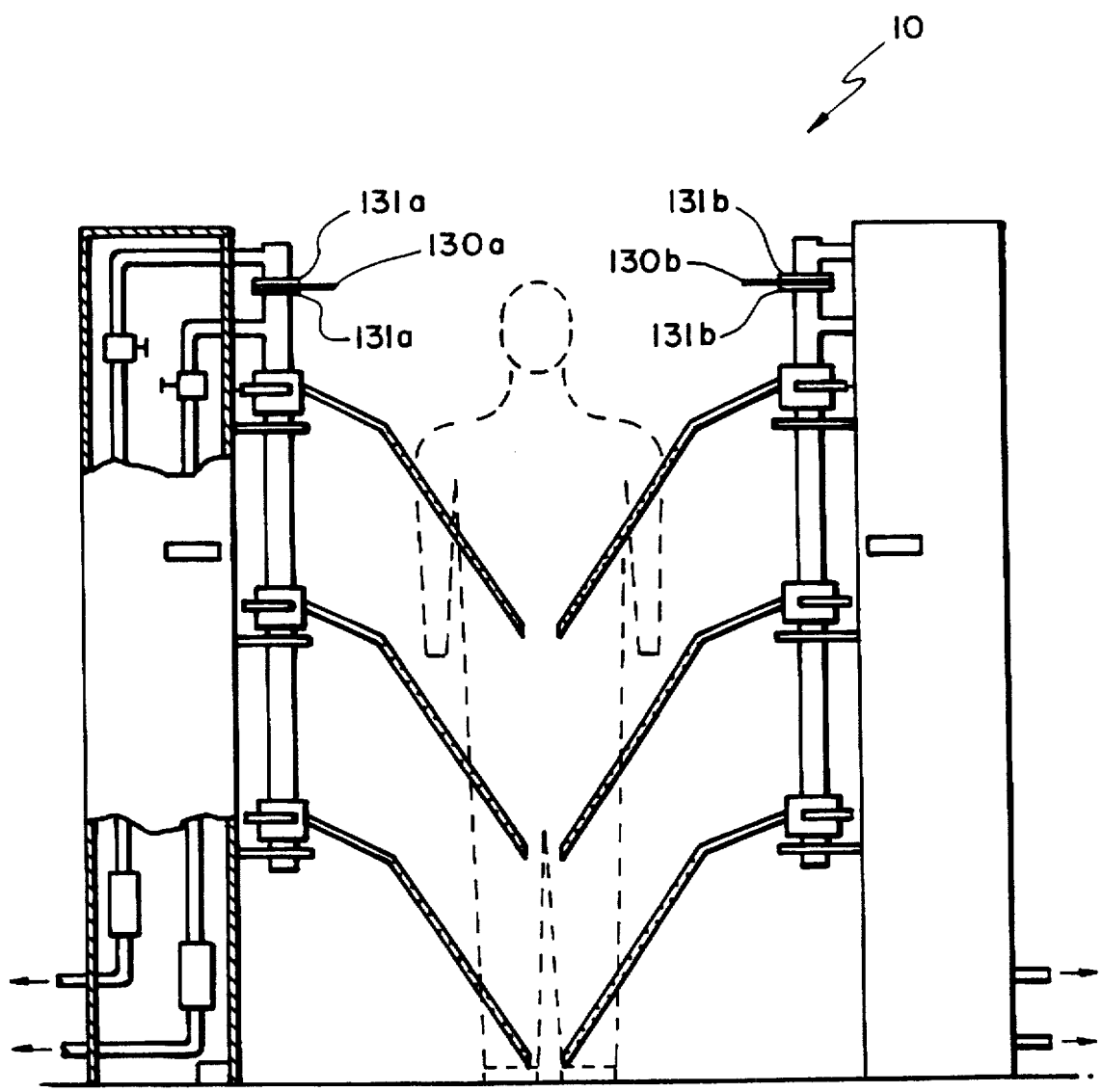
FIG. 9 is a partially cut away front view of a different vapor and particle collector installed in the explosives sampling system of FIG. 1.
Figure 10:
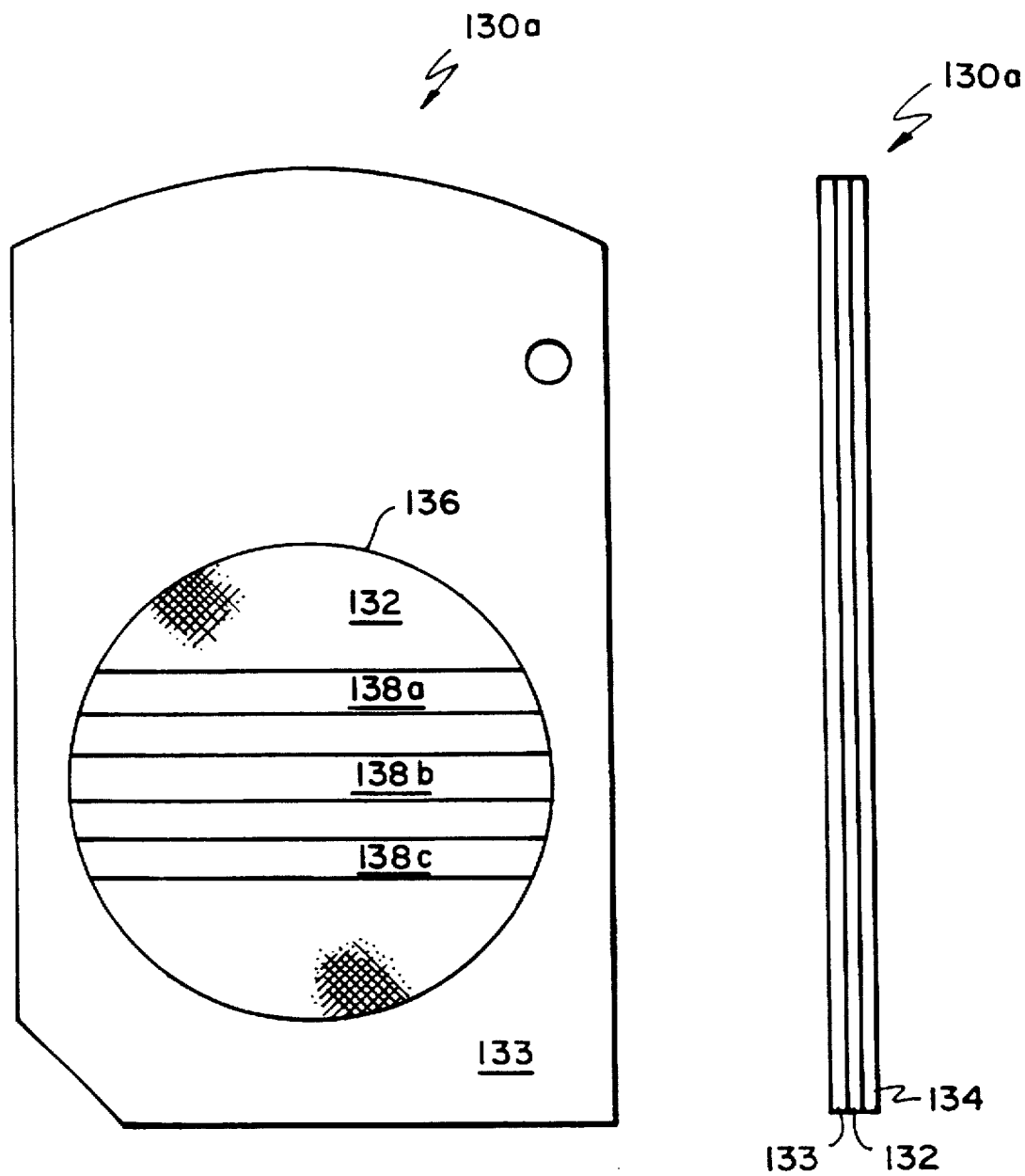
FIG. 10a is a front view of the vapor and particle collector of FIG. 9.
FIG. 10b is a side view, not to scale, of the vapor and particle collector of FIG. 9.

Moreover, the collector may be of any of a number of types, in addition to those disclosed in U.S. Pat. No. 5,092, 217. For instance, as shown in FIG. 9, in some applications it may be preferable to substitute a filter paper ticket 130a, 130b, held fixed in system 10 by a pair of clamps 131a, 131b, for collectors 44a, 44b. As shown in FIGS. 10a and 10b, filter paper ticket 130a (filter paper ticket 130b is identical to filter paper ticket 130a) includes a piece of filter paper 132 laminated between two sheets 133, 134 of quasi-rectangular card stock. (Filter paper ticket 130a is not shown to scale in FIG. 10b.) The filter paper, the card stock, and the adhesive used to laminate them together should not, when heated, emit vapors that have gas chromatography signatures similar to the explosive substances of interest. A low-lint, cellulose-based filter paper, such as Crystal No. 8, available from H. L. Bouton Co., 320 Main Street, Buzzards Bay, Mass. has been found to be suitable. The card stock can be 0.010 in. (0.025 cm) TAG, or manilla, paper, and the adhesive can be an air-dry, pressure-sensitive silicone adhesive, available from Minnesota Mining and Manufacturing, Co.

When filter paper ticket 130a is laminated together, filter paper 132 completely covers an approximately 1.5 in. (3.5 cm.) diameter hole 136 in each piece of card stock 133, 134. Three parallel strips of self-adhesive polyimide tape 138a, 138b, 138c, such as Scotchbrand·No. 5413 tape, available from Minnesota Mining and Manufacturing, Co., are applied to one of the filter paper surfaces. Generally, filter paper tickets 130a, 130b are installed in system 10 (between clamps 131a, 131b) so that polyimide strips 138a, 138b, 138c are facing the direction of airflow (i.e., the exposed, non-adhesive surface of strips 138a, 138b, 138c face into the flow).

Polyimide has been found to exhibit a high affinity for explosives vapors. The polyimide strips are substantially gas impermeable, in that although explosives vapors can diffuse into or adhere onto the polyimide, there is essentially no mass flow through the strips. Several considerations factor into the selection of the number, width, and spacing of the polyimide strips. The greater the percentage of the filter paper surface area covered by the polyimide strips, the larger the region to which explosives vapors can bind, but the smaller the total flow area of the ticket (and thus, the greater the pressure drop across the ticket). Furthermore, the wider the polyimide strips, the larger the "dead space," or boundary layer, near the centers of the strips, as the airflow separates to go around the strips and through the filter paper. This boundary layer may prevent explosives vapors from coming sufficiently close to the strips to bind to them. Balancing these considerations, it has been found suitable to use three 0.125 in. (0.30 cm.) wide strips 138a, 138b, 138c, separated by 0.125 in. (0.30 cm), to cover approximately 25% of the filter paper surface.

In operation, filter paper tickets 130a, 130b are used in system 10 in essentially the same manner as collectors 40a, 40b. As vacuum blowers 48a, 48b draw sample air through the tickets, at least a portion of the explosives vapors intermixed with the sample air binds with polyimide strips 138a, 138b, 138c, and at least a portion of the explosives particles entrained in the sample air stream become trapped in the fibers of filter paper 132. When the sample cycle has concluded, tickets 130a, 130b are removed from the system 10 and inserted into a ticket desorb assembly 142.

Figure 11:
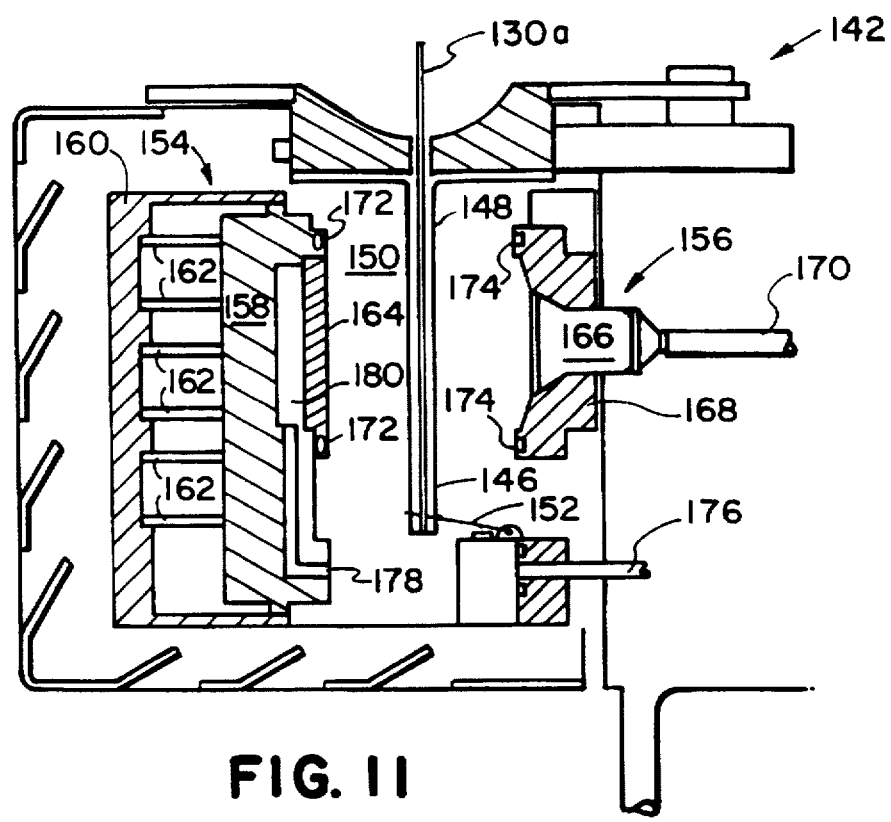
FIG. 11 is a partially cut away side view of a ticket desorb assembly for use with the vapor and particle collector of FIG. 9, showing the ticket desorb assembly in the open position.
Figure 12:
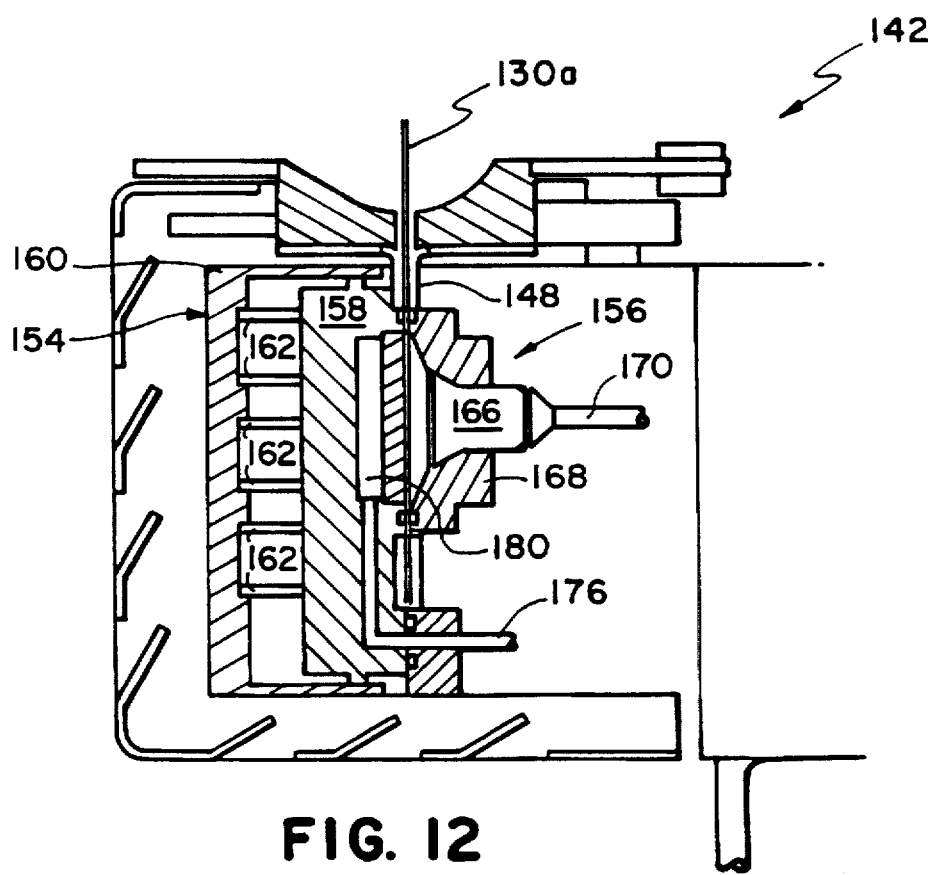
FIG. 12 is a partially cut away side view of a ticket desorb assembly for use with the vapor and particle collector of FIG. 9, showing the ticket desorb assembly in the closed position.

As shown in FIGS. 11, and 12, in particular ticket 130a is inserted into a slot 146 in a sheet metal guide 148 fixed to the walls of a filter paper guide 150 in the interior of the desorb assembly 142. Ticket 130a is shown only partially inserted into assembly 142 in FIG. 11. When fully inserted, ticket 130a triggers a microswitch 152 at the bottom of guide 148, activating a motor (not shown). A cam and cam follower assembly (not shown) driven by the motor force filter paper guide 150 and a back plate assembly 154 toward a snout assembly 156. As shown in FIG. 11, when assembly 142 is in the open position, back plate assembly 154 is approximately twice as far from snout assembly 156 as filter paper guide 150. Accordingly, the cam and cam follower assembly are configured to move filter paper guide 150 at about half the speed as back plate assembly 154.

Back plate assembly 154 includes a machined aluminum block 158 slidably mounted within a frame 160, with two columns of three springs 162 (only one column shown) located between the back side of block 158 and frame 160. A sintered, stainless steel disk 164 is pressed into a mating recess in the front surface of block 158. An electrical resistance heater (not shown) surrounds disk 164.

Snout assembly 156 includes a snout 166 supported by a snout frame 168. An electrical resistance heater (not shown) surrounds snout 166. A desorb gas delivery line 170 extends from the front end of the snout, supplying desorb air from desorb assembly 142 to, for example, a high-speed gas chromatograph (not shown).

In operation, disk 164 and snout 166 are preheated before ticket 130a is inserted into desorb assembly 142. Ticket 130a is inserted into the desorb assembly with polyimide strips 138a, 138b, 138c (FIG. 10a) facing sintered disk 164. When block 158 and ticket 130a are driven into contact with snout assembly 156 by the motor, cam, and cam follower assembly, as shown in FIG. 12, springs 162 compress slightly to provide a desired contact force between block 158 and snout frame 168. Block 158 can also pivot slightly within frame 160, allowing it to align parallel to snout frame 168. O-rings 172, 174 in block 158 and snout frame 168 provide a substantially airtight seal between back plate assembly 154, ticket 130a, and snout assembly 156.

With desorb assembly 142 closed, dry air is supplied through a supply line 176 and a passage 178 in block 158 to a plenum chamber 180 behind disk 164. The air is heated as it passes through the heated sintered disk. The combination of the heated air and the heat radiated by the heated disk and the heated snout vaporizes substantially all explosives vapors and particles trapped in filter paper ticket 130a. The vapor-laden desorb air passes through snout 166 and delivery line 170 into the high-speed gas chromatograph for analysis. Because filter paper ticket 130a is inserted into desorb assembly 142 with polyimide strips 138a, 138b, 138c facing disk 164, the desorb air flows through filter paper ticket 130a in the same direction as did the sample air when the ticket was installed in system 10. Thus, dirt or other foreign matter that does not vaporize at low temperature will remain trapped in the filter paper fibers, and will not be carried into the gas chromatograph.

Figure 13:
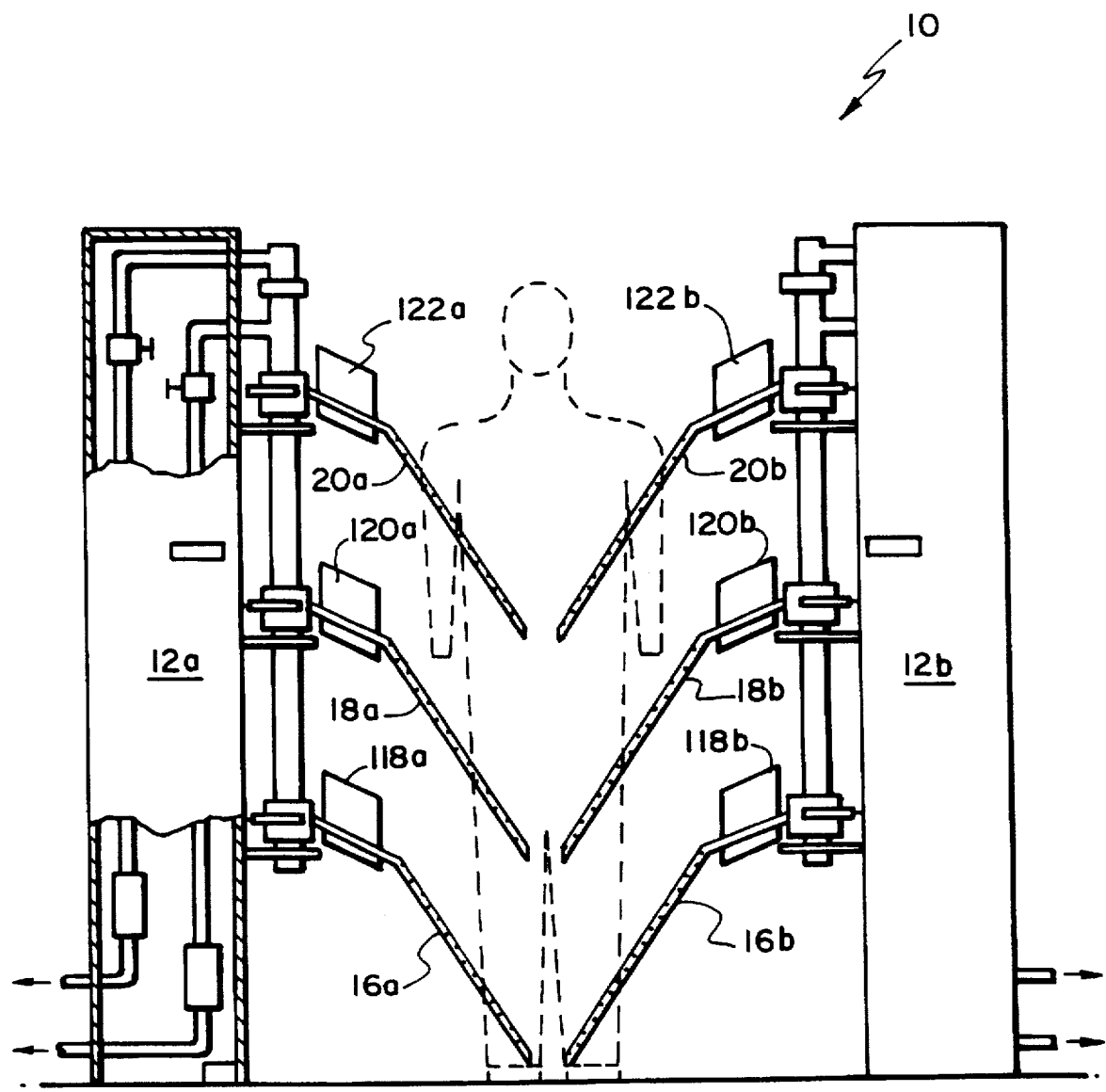
FIG. 13 is a partially cut away front view of another explosives sampling system.

As shown in FIG. 13, panels 118a, 120a, 122a; 118b, 120b, 122b may be attached to the portions of wands 16a, 18a, 20a, 16b, 18b, 20b that lie closest to housings 12a, 12b. Studies have shown that panels thus located may cause some people to rotate 90° as they walk through system 10. The wands then sample the person's front and back, which are generally of larger surface area than his sides.

Figure 14:
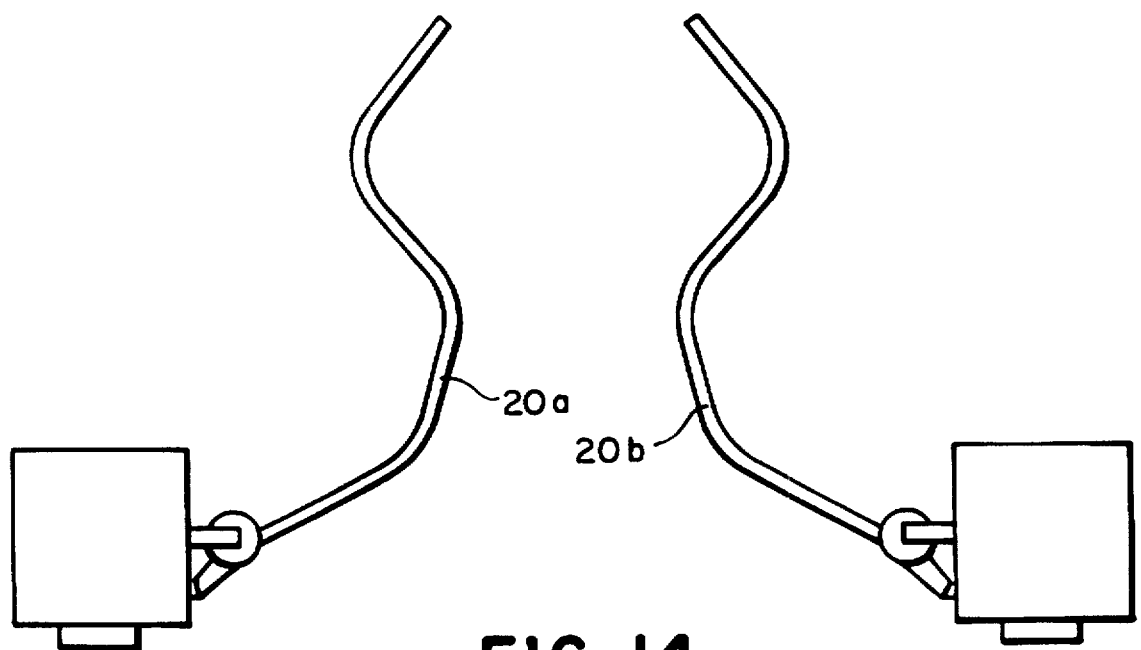
FIG. 14 is a top view of another explosives sampling system.

Moreover, the wands, which need not be tubes but can be of any cross section, can be bent into a number of different shapes other than those shown and described above. For instance, when viewed from the top, the wands may be S-shaped, as shown in FIG. 14 (only wands 20a, 20b shown). Generally, the shape of the wand will be selected in accordance with the body shape of the typical subject. Thus, if the typical subject has a fairly round waist, the bows in the S-shaped wands would tend to encircle the subject's waist as the wands sweep down to that region, placing a greater number of holes in contact with the subject. In addition, brushes or puffers (i.e., jets that deliver shorts bursts of air) can be located near all or some of holes 22 in wands 16a, 18a, 20a; 16b, 18b, 20b to help dislodge particles from the subject's hair, skin, clothing, etc. It may also be beneficial to include a small contact valve in the opening each of holes 22. As the subject contacts them, the valves open, providing a fluid flow passage to the interior of the wands.

And although in the embodiments shown and described above pivot mechanisms attach the wands to the housings, if the wands themselves are sufficiently flexible, they can be attached directly to the manifold assemblies. As a person walks through the system, the wands flex as necessary, following the contours of his body.

Moreover, the vapor and particle sampling systems described herein can be used to sample other subjects, such as luggage or food products. If so, the dimensions, orientations, positions, and number of wands, holes, and orifices may be tailored to best match the surface contour and other characteristics of the subject. The system can also be used for other than explosives sampling applications. For instance, the system may be configured to collect particles and vapors from other contraband, such as narcotics and perfumes, or, in the food processing industry, from animal or vegetable matter, such as chicken, beef, or fish, for example to detect decay or contamination.

What is claimed is:

1. Apparatus for collecting vapor or particles from a surface of a subject moving in a substantially linear direction with respect to said apparatus, said apparatus comprising:
   a housing;
   a wand pivotally mounted to said housing said wand being arranged to contact said surface of said subject and having a central fluid flow passage extending along a longitudinal axis of said wand;
   a plurality of holes disposed in a wall of said wand, each of said holes providing a fluid flow passage between atmosphere and said central fluid flow passage of said wand;
   said wand mounted to said housing so that said holes extend in said direction of movement of said subject;
   a vacuum source in fluid communication with said central fluid flow passage of said wand for drawing a sample of working fluid through said fluid flow passages provided by said plurality of holes; and
   a collector in fluid communication with said central fluid flow passage of said wand to collect vapor or particles intermixed in said sample of working fluid.

2. The apparatus of claim 1 wherein an external width of said wand is less than a characteristic dimension of the contour of said surface of said subject.

3. The apparatus of claim 2 wherein said subject is a person.

4. The apparatus of claim 3 wherein said external width of said wand is less than about 10 cm.

5. The apparatus of claim 1 further comprising a plurality of said wands.

6. The apparatus of claim 5 wherein a first one of said wands is mounted to a first portion of said housing and a second one of said wands is mounted to a second portion of said housing, wherein said subject moves between said first and said second portions of said housing.

7. The apparatus of claim 6 wherein said first one of said wands is biased toward said second one of said wands.

8. A collector for collecting explosives vapor and particles intermixed in a sample air stream, said collector comprising:
   a section of substantially gas permeable filter paper comprising fibers interwoven to trap at least some of said explosives particles as said sample air stream passes through said filter paper; and
   a substantially gas impermeable material exposed on a surface of said filter paper, said material having a high binding affinity for said explosives vapor.

9. Apparatus for collecting vapor or particles from a surface of a subject moving in a substantially linear direction with respect to said apparatus, said apparatus comprising:
   a housing;
   a wand pivotally mounted to said housing, said wand being arranged to contact said surface of said subject and having a central fluid flow passage extending along a longitudinal axis of said wand, an end of said central fluid flow passage being open to atmosphere;
   a plurality of holes disposed in a wall of said wand, each of said holes providing a fluid flow passage between atmosphere and said central fluid flow passage of said wand;
   said wand mounted to said housing so that said holes extend in said direction of movement of said subject;
   a vacuum source in fluid communication with said central fluid flow passage of said wand for drawing a sample of working fluid through said fluid flow passages provided by said plurality of holes; and
   a collector in fluid communication with said central fluid flow passage of said wand to collect vapor or particles intermixed in said sample of working fluid.

10. The apparatus of claim 9 further comprising an orifice disposed in said open end of said central fluid flow passage.

11. The apparatus of claim 1 wherein said wand is pivotally mounted to said housing.

12. The apparatus of claim 11 further comprising a damper for damping the rotation of said wand.

13. The apparatus of claim 1 wherein said longitudinal axis of said wand is curved.

14. The apparatus of claim 1 wherein said wand is comprised of a tubular section.

15. The apparatus of claim 1 wherein said wand is comprised of polyvinyl chloride.

16. The apparatus of claim 1 wherein each of said plurality of holes is oriented at an acute angle with respect to said longitudinal axis of said wand.

17. The apparatus of claim 1 wherein said holes are disposed at different rotational orientations around the circumference of said wall of said wand.

18. Apparatus for collecting vapor or particles from a surface of a subject moving in a substantially linear direction with respect to said apparatus said apparatus comprising:

a housing;

a wand having a central fluid flow passage extending along a longitudinal axis of said wand;

a plurality of holes disposed in a wall of said wand each of said holes providing a fluid flow passage between atmosphere and said central fluid flow passage of said wand;

said wand mounted to said housing so that said holes extend in said direction of movement of said subject;

a vacuum source in fluid communication with said central fluid flow passage of said wand for drawing a sample of working fluid through said fluid flow passages provided by said plurality of holes;

a collector in fluid communication with said central fluid flow passage of said wand to collect vapor or particles intermixed in said sample of working fluid; and a bypass line in fluid communication with said central fluid flow passage for removing a portion of said sample of working fluid from said central fluid flow passage before said sample of working fluid reaches said collector.

19. The apparatus of claim 1 further comprising a valve in said bypass line for adjusting the size of the portion of said sample of working fluid removed from said central fluid flow passage.

20. The apparatus of claim 1 wherein said subject is a person.

21. The apparatus of claim 1 wherein said collector is configured for use with an explosives vapor analyzer.

22. Apparatus for collecting vapor or particles from a surface of a moving subject, said apparatus comprising:

a housing;

a wand pivotally mounted to said housing, said wand being arranged to contact said surface of said subject and having a central fluid flow passage extending along a longitudinal axis of said wand, said longitudinal axis of said wand being oriented at an acute angle with respect to a direction of movement of said subject through said apparatus, an external width of said wand being less than a characteristic dimension of the contour of said surface of said subject;

a plurality of holes disposed in a wall of said wand, each of said holes providing a fluid flow passage between atmosphere and said central fluid flow passage of said wand;

a vacuum source in fluid communication with said central fluid flow passage of said wand for drawing a sample of working fluid through said fluid flow passages provided by said plurality of holes; and a collector in fluid communication with said central fluid flow passage of said wand to collect vapor or particles intermixed in said sample of working fluid.

23. The apparatus of claim 22 wherein said subject is a person.

24. The apparatus of claim 23 wherein said width of said wand is less than about 10 cm.

25. Apparatus for collecting particles from a moving surface, said apparatus comprising:

a housing;

a wand pivotally mounted to said housing, said wand being arranged to contact said surface and having a central fluid flow passage extending along a longitudinal axis of said wand, said longitudinal axis of said wand being oriented at an acute angle with respect to a direction of movement of said surface through said apparatus;

a plurality of holes disposed in a side wall of said wand, each of said holes providing a working fluid flow passage between atmosphere and said central fluid flow passage of said wand;

a vacuum source in fluid communication with said central fluid flow passage of said wand for drawing a sample of working fluid through said working fluid flow passages;

a collector in fluid communication with said central fluid flow passage of said wand to collect particles entrained in said sample of working fluid; and said central fluid flow passage being sufficiently wide to prevent substantially all particles of on the order of about 10 microns in diameter from colliding with said wall of said wand after said particles enter said central fluid flow passage from said working fluid flow passages.

26. The apparatus of claim 25 wherein each of said plurality of holes is oriented at an acute angle with respect to said longitudinal axis of said wand.

27. The apparatus of claim 25 wherein an end of said central fluid flow passage is open to atmosphere.

28. The apparatus of claim 27 further comprising an orifice disposed in said open end of said central fluid flow passage.

29. The apparatus of claim 25 wherein the width of said central fluid flow passage is greater than about 1.0 cm.

30. A system for collecting vapor from a subject moving in a substantially linear direction with respect to said system, said system comprising:

first and second housings;

first and second symmetrically disposed arrays of sampling wands projecting from said respective first and second housings to contact said subject as said subject moves with respect to said system, each of said sampling wands having a central fluid flow passage;

said sampling wands disposed at an acute angle to said direction of movement of said subject to traverse a surface of said subject as said subject moves with respect to said system;

a sampling hole in each of said wands providing a working fluid flow passage between atmosphere and said associated central fluid flow passage;

a vacuum source in fluid communication with at least some of said central fluid flow passages for drawing a sample of working fluid through at least some of said working fluid flow passages;

a collector in fluid communication with said vacuum source to collect vapor entrained in said sample of working fluid.

31. The collector of claim 8 wherein said fibers of said filter paper comprise cellulose.

32. The collector of claim 8 wherein said material comprises polyimide.

33. The collector of claim 8 wherein said material is arranged in strips on said surface of said filter paper.

34. The collector of claim 8 wherein said filter paper is held in a frame.

* * * * *